United States Patent [19]

Coates

[11] Patent Number: 5,244,454
[45] Date of Patent: Sep. 14, 1993

[54] DEVICE FOR ASSISTING AND MAINTAINING PENILE ERECTION

[76] Inventor: Graham Coates, 1112 N. Madison St., Albany, Ga. 31708-3401

[21] Appl. No.: 995,600

[22] Filed: Dec. 14, 1992

[51] Int. Cl.⁵ ............................................... A61F 5/41
[52] U.S. Cl. .................................................... 600/41
[58] Field of Search .............................. 600/38, 39, 41

[56] References Cited

U.S. PATENT DOCUMENTS

| | | |
|---|---|---|
| 3,461,863 | 8/1969 | Sullinger . |
| 3,511,230 | 5/1970 | Strong ................................. 600/41 |
| 3,926,184 | 12/1975 | Gehl . |
| 4,643,175 | 2/1987 | Chapman . |
| 4,653,484 | 3/1987 | Cannon . |
| 4,724,829 | 2/1988 | Knapps . |
| 4,785,802 | 11/1988 | Blount .................................. 600/39 |
| 5,027,800 | 7/1991 | Rowland . |

FOREIGN PATENT DOCUMENTS 547535   9/1942  United Kingdom ................... 600/39

*Primary Examiner*—Cary E. O'Connor
*Attorney, Agent, or Firm*—James A. Hinkle

[57] ABSTRACT

A penile engorgement valve has a looped rod (1) with an arcuate center section (2) positioned on a top base surface of a male penis (3). Opposite side sections (5) of the looped rod are extendable arcuately at opposite sides of the male penis and juxtaposed at a fulcrum curve (6) in each of the opposite side sections. A lever arm (7) is extended from the fulcrum curve in each juxtaposed side section and attachable to a tension member (11). The tension member is anchored to a hip section and rearward of a user. Tension from the tension member is applied to the lever arms in a direction towards the hip section of the user. The tension results in pressure on the fulcrum curves and on the arcuately looped center. Blood flows into the penis in arteries (16) and returns in flow out from the penis in veins (15) at the top of the penis in a public area (4) where the arcuately looped center is positioned and at opposite bottom sides of the penis in a perineal area (8) where the fulcrum curves are positioned. Flow of blood out from the penis is restricted relatively more than flow of blood into the penis by a valvular effect resulting from relatively greater collapsibility of the veins than of the arteries from the pressure applied. This enhances penile engorgement and turbidity for sexual intercourse. Pressure adjustment and cushioning on of the looped rod are included.

20 Claims, 3 Drawing Sheets

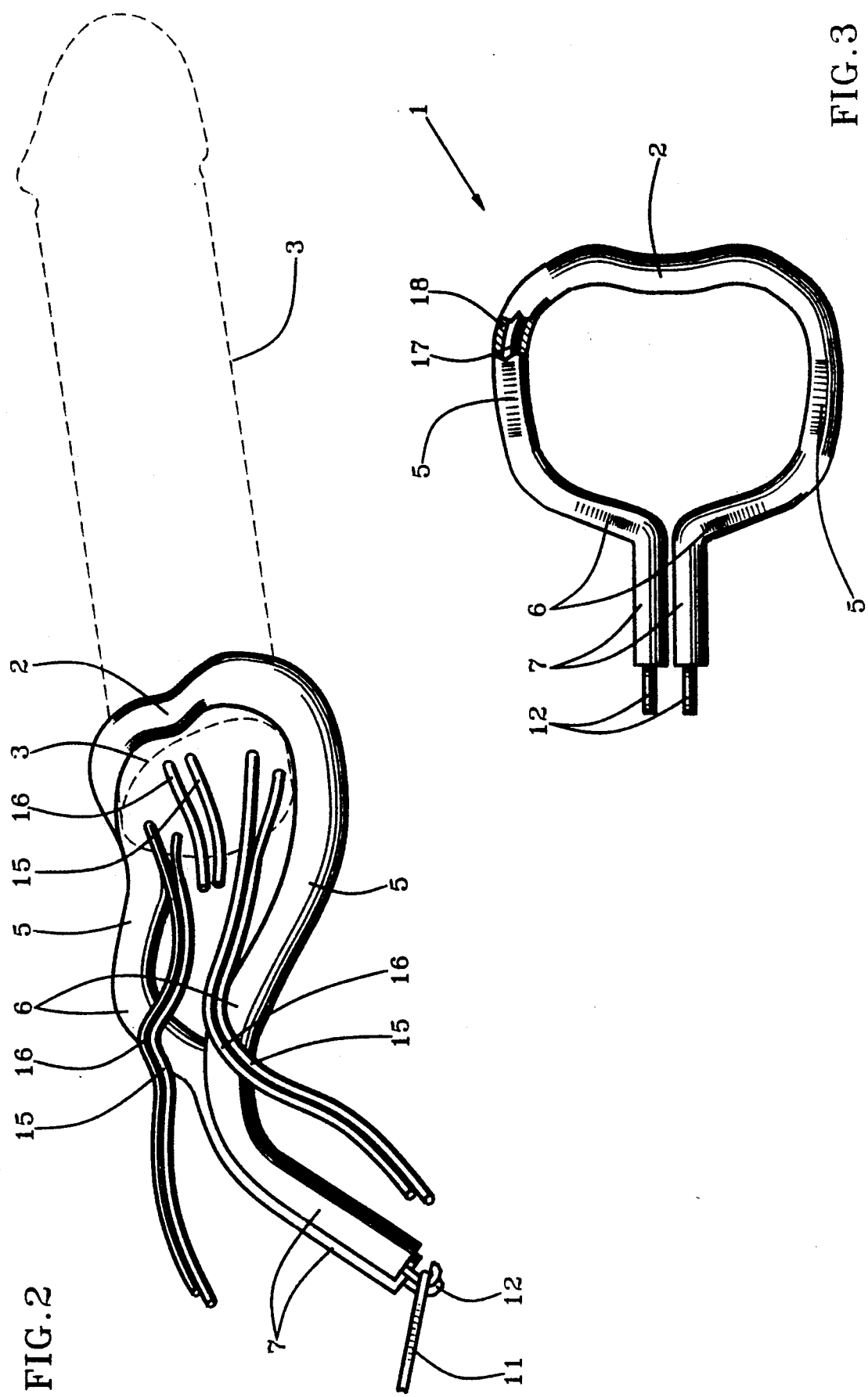

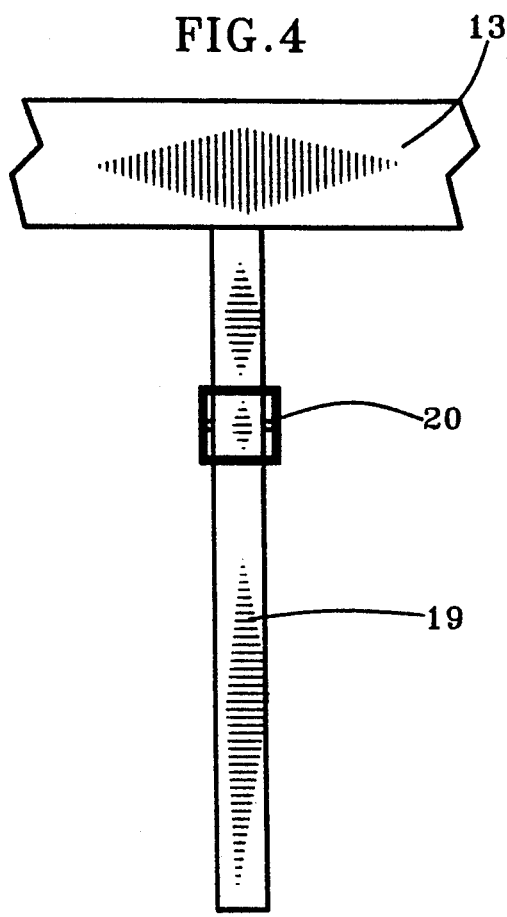
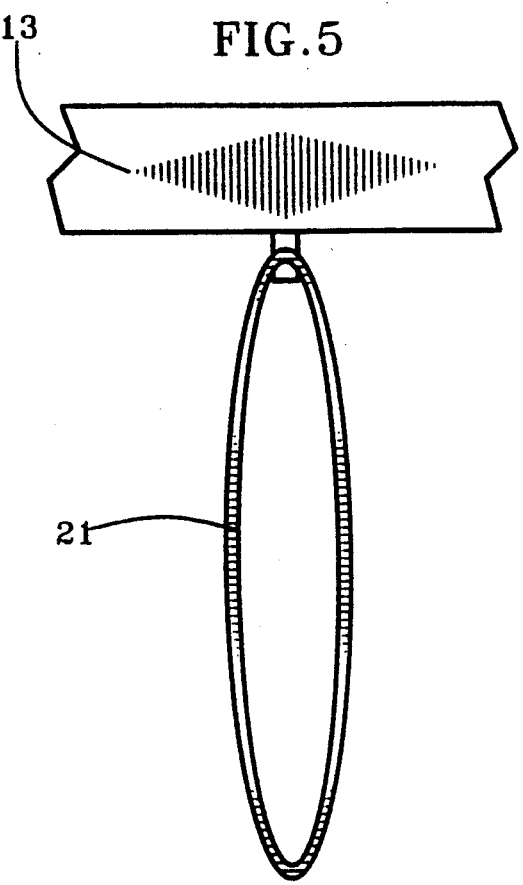
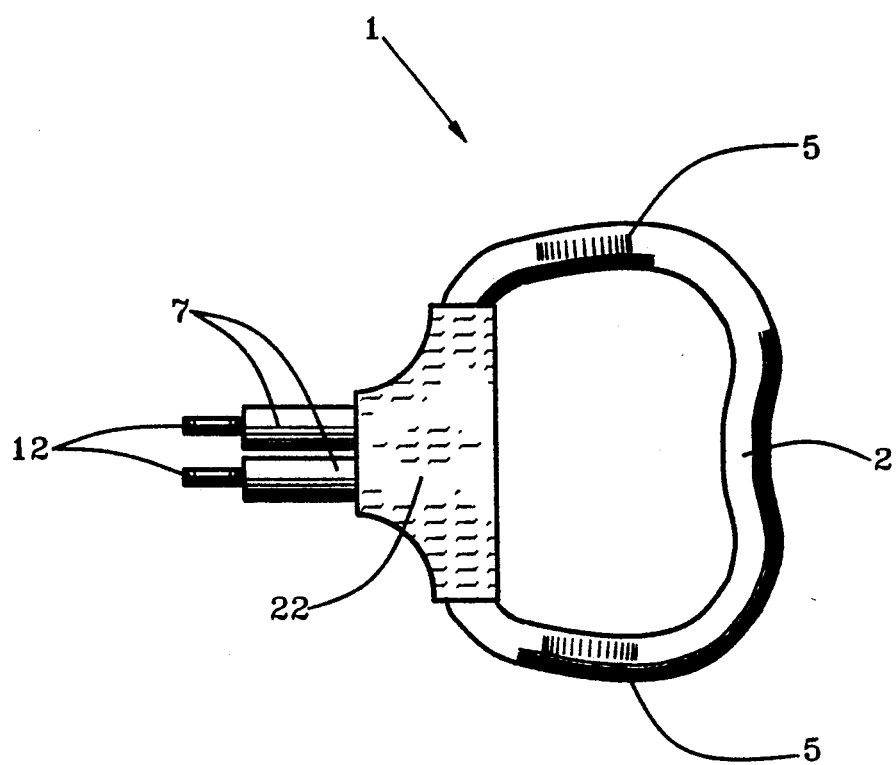
FIG.6

DEVICE FOR ASSISTING AND MAINTAINING PENILE ERECTION

BACKGROUND OF THE INVENTION

I. Field of the Invention

The present invention relates generally to the field of penile erection support means. In particular, it is a pressure valve positioned externally on the one pubic and the two perineal areas of arterial entry of blood into and veinal exit of blood out from the penis. Application of external pressure sufficient to squeeze the easily collapsible exit veins closed, but insufficient to close the less collapsible entry arteries, increases blood pressure in the penis with a valvular effect to aid in achieving and maintaining penile erection during sexual intercourse.

II. Description of the Prior Art

It has been known since the early era of modern medicine that valvular control of blood flowing in and out of the penis could be employed to aid in achieving adequate turgidity for successful coitus. There have been a variety of valvular devices to accomplish this objective. None, however, have provided precise positioning of an external pressure valve on all three areas of arterial entry into and veinal exit out from the penis. Nor has any known device provided variable pressure that can be regulated by a user on all three blood flow areas effectively in a manner taught by this invention.

Typical of devices in the prior art are resilient bands positioned around the base of the penis as described in U.S. Pat. No. 5,027,800 granted to H.L. Rowland on Jul. 2, 1991 and Number 3,461,863 granted to G.R. Sullinger on Aug. 19, 1969. A penile cylinder supported by belts to apply pressure to only one blood flow area at the base of the penis was described in U.S. Pat. No. 4,724,829 granted to O.L. Knapps on Feb. 16, 1988. An elastic cord that encircled the waist and passed between the legs from the rear of a user to engage a rigid arc member on top of the penis to provide pressure on only the pubic blood flow area was taught by U.S. Pat. No. 4,643,175 granted to K. Chapman on Feb. 17, 1987. A penile support splint without any valvular means was described in U.S. Pat. No. 4,653,484 granted to L.J. Cannon on Mar. 31, 1987. Neither of these devices nor any other known device is believed to describe or to teach the three point valvular control of penile blood flow provided by this invention.

Impotency is typically caused by valvular dysfunction resulting from the aging process, psychosomatic causes, cultural inhibitions and various environmental stresses. Some impotency is caused by physical injury or illness. Impotency is usually aggravated by aging. Regardless of the cause, however, it has a major adverse effect on marital relations and on resulting societal conditions. Although this invention does not reverse causes of the dysfunction, it has remedial utility.

SUMMARY OF THE INVENTION

In accordance with the present invention, it is contemplated that the primary object of this invention is to provide external valvular control of penile blood flow which allows arterial flow into but restricts veinal flow out from the male penis to aid individuals having penile valvular dysfunction in achieving penile engorgement during sexual intercourse.

Another object is to provide external control of penile blood flow with variable pressure for individual needs.

Yet another object is to provide an external penile blood flow valve which is comfortable, convenient to use, nonobstructive of sexual intercourse, aesthetically unoffensive and inexpensive.

This invention accomplishes the above and other objectives with a looped rod having an arcuate center section positioned on a top base surface of a male penis. Opposite side sections of the looped rod are extendable arcuately at opposite sides of the male penis and juxtaposed at a fulcrum curve in each of the opposite side sections. A lever arm is extended from the fulcrum curve in each juxtaposed side section and attachable to a tension member. The tension member is anchored to a hip section of a user. Tension from the tension member is applied to the lever arms in a direction towards the hip section and rearward of the user. The tension results in pressure on the fulcrum curves and on the arcuately looped center. Blood flows into the penis in arteries and returns in flow out from the penis in veins at the top of the penis in a pubic area where the arcuately looped center is positioned and at opposite bottom sides of the penis in a perineal area where the fulcrum curves are positioned. Flow of blood out from the penis is restricted relatively more than flow of blood into the penis by a valvular effect resulting from relatively greater collapsibility of the veins than of the arteries from the pressure applied. This enhances penile engorgement and turbidity from sexual arousal for sexual intercourse. In addition, the penis can erect from the mechanics of the valvular action produced by the invention, and without mental and external excitement. Pressure adjustment and cushion on of the looped rod are included.

Other objects, advantages and capabilities of the invention will become apparent from the following description taken in conjunction with the accompanying drawings showing preferred embodiments of the invention.

BRIEF DESCRIPTION OF THE DRAWINGS

FIG. 2 is a perspective view illustrating relationship of the valve to arteries and veins of a penis;

FIG. 3 is a top view without a tension member and tension anchor;

FIG. 4 is a rear view of a tension anchor belt and a tension member strap with a length adjustment buckle;

FIG. 5 is a rear view of a tension anchor belt and a tension member rubber band; and FIG. 6 is a bottom view with an optional cushion pad on a fulcrum curve of the valve.

DESCRIPTION OF THE PREFERRED EMBODIMENT

Figure 1:
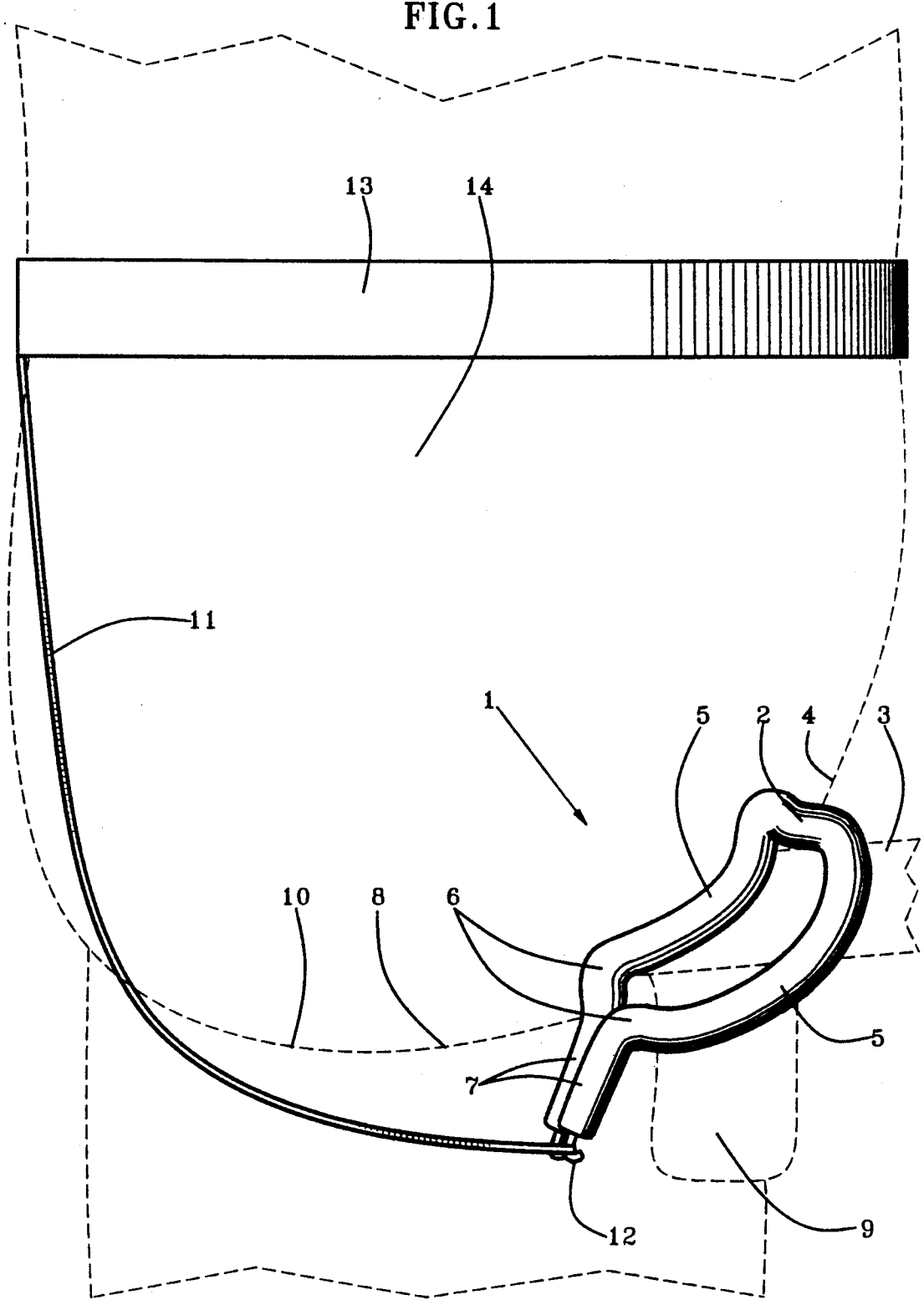
FIG. 1 is a perspective side view illustrating this penile engorgement valve in relation to the related parts of a male shown in broken lines.

Referring to the drawings wherein like reference numerals designate corresponding parts throughout the several figures, a looped rod 1 has an arcuate center section 2 positioned on top of a penis 3 proximate a pubic section 4 of a user. From the arcuate center section 2, opposite side sections 5 are extended arcuately at opposite sides of the penis 3 and juxtaposed at a fulcrum curve 6 where a lever arm 7 is extended downwardly and rearwardly in relation to a perineal area 8 of a user in a standing position. The opposite side sections 5 are separated a sufficient distance to allow comfortable entry of the penis 3 and scrotum 9 of the user. In the perineal area between the scrotum and the anus 10, the opposite side sections 5 are arched into the fulcrum curve 6. A tension member 11 is attachable to tension attachment means 12 on a terminal end of each lever arm 7 at one end of the tension member 11 and attachable to a tension anchor 13 such as a belt. The tension anchor 13 is attachable to a hip section 14 of the user. Tension of the tension member 11 in a generally rearward and upward direction supported by surface area of the user proximate the anus 10 leverages pressure on the fulcrum curves 6 and on the arcuate center 2 at an opposite side of the fulcrum curves 6 from the lever arms 7.

Referring to FIGS. 1 and 2, penile veins 15 are closed while penile arteries 16 are left open with an equal amount of select pressure applied to both at opposite sides of the perineal area 8 and on top of the penis 3 proximate the pubic area 4. It is preferable that the amount of pressure be variable according to tension pressure of the tension member 11 in order to be most effective for different individuals. The pressure that the arteries 16 and veins 15 experience must be a value between an individual's venous pressure and arterial pressure. For example, if venous pressure is 40 mm Hg and arterial pressure is 140 mm Hg, pressure between 40 and 140 mm Hg on the vessels 15 and 16 would produce a valvular action. A pressure greater than 40 mm Hg would collapse the veins 15 and thereby prevent venous flow while allowing the penis to fill because the same amount of pressure would not be enough to block arterial flow through arteries 16. The higher the pressure over the vein 15 and artery 16 u to but not exceeding sufficient pressure to close the artery 16, the easier and better an erection is maintained.

Referring to FIG. 3, a top view of the looped rod 1 shows the arcuate center 2 relatively close to the fulcrum curves 6 as a result of relative length of the opposite side sections 5 in a slanted attitude. The looped rod 1 can be a metallic member 17 covered by cushioning material 18 such as surgical tubing. The looped rod 1 can be produced in different sizes for different individuals or shaped by bending beyond a critical bending point of the metallic member 17 for tailoring it to particular individuals.

It may be that, in certain individuals, the rod 17 and tubing cushioning 18 may not provide the desired comfort to the user. Therefore, it is contemplated that the tubing cushioning 18 may have an enlarged diameter to accomodate a fluid reservoir that would allow the cushioning 18 to conform more readily to the users anatomy, while still providing the needed pressure by the accompanying rod 17.

Referring to FIGS. 1 and 4, a resilient strap 19 with a length adjustment buckle 20 can be attachable to the tension anchor 13 and to the tension attachment means 12. It provides a convenient means for varying tension and resulting pressure on the fulcrum curves 6 and on the arcuate center 2. The strap 19 can be made an optimum width between legs of a user as desired.

Referring to FIG. 5, an elastic band 21 can be used as a tension member 11. A select plurality of elastic bands can be used to increase pressure. Alternatively, the elastic bands can be different lengths and have different resiliencies for desired tension.

Referring to FIG. 6, a cushion pad 22 can be positioned on a bottom surface of the looped rod 1 proximate the fulcrum curves 6 and their confluence with the lever arms 7 to increase comfort as may be desired for some individuals. However, the pad 22 should not be broad and thick enough to disperse pressure over too broad an area or valvular action in proportion to pressure applied will be diminished.

Various modifications may be made of the invention without departing from the scope thereof and it is desired, therefore, that only such limitations shall be placed thereon as are imposed by the prior art and which are set forth in the appended claims.

What is claimed is:

1. A penile engorgement valve comprising:
   a looped rod having an arcuately looped center positioned proximate a pubic area on a top base surface of a male penis,
   opposite side sections of the looped rod extended arcuately to a fulcrum curve of each opposite side section with each fulcrum curve positioned on a perineal area of a user at an opposite side of a perineal base of the male penis,
   a lever arm extended from each fulcrum curve in an angular direction that is rearward and downward from the perineal base of the male penis and between legs of the user when the user is in a standing position,
   a tension member attachable to the lever arms, and
   a tension anchor attachable to the tension member and attachable to a hip section of the user.

2. A penile engorgement valve as claimed in claim 1 and further comprising:
   a pubic base projection on an inside periphery of the arcuately looped center of the looped rod, and
   the pubic base projection being sized and shaped to contact the top base surface of the male penis.

3. A penile engorgement valve as claimed in claim 2 wherein the pubic base projection is a reverse curve extended inwardly from the arcuately looped center of the looped rod.

4. A penile engorgement valve as claimed in claim 1 wherein the looped rod is spring metal coated with a cushioning material.

5. A penile engorgement valve as claimed in claim 4, wherein the cushioning material encloses a fluid filled cavity.

6. A penile engorgement valve as claimed in claim 1 and further comprising:
   a tension member hook on distal ends of the lever arms.

7. A penile engorgement valve as claimed in claim 6 wherein the tension member is an elastic band positioned on the tension member hook on distal ends of the lever arms and attachable to the tension anchor.

8. A penile engorgement valve as claimed in claim 6 wherein the tension member is a select plurality of elastic bands positioned on the tension member hook and attachable to the tension anchor, and
   the plurality of elastic bands being determined by tension required to provide desired pressure of the fulcrum curve and of the looped center on proximate veins and arteries.

9. A penile engorgement valve as claimed in claim 1 wherein the tension anchor is a flexible belt positioned on the hip section of the user.

10. A penile engorgement valve as claimed in claim 1 wherein the tension member is a resilient strap.

11. A penile engorgement valve as claimed in claim 10 and further comprising:
a length adjustment buckle with which the resilient strap is adjustable in length and attachable to the tension anchor.

12. A penile engorgement valve as claimed in claim 11 wherein the tension anchor is a flexible belt positioned on the hip section of the user.

13. A penile engorgement valve as claimed in claim 1 and further comprising:
a cushion pad positioned on the fulcrum curves between the looped rod and the perineal area of the user.

14. A penile engorgement valve comprising:
a looped rod having an arcuately looped center positioned proximate a pubic area on a top base surface of a male penis,
a pubic base projection on an inside periphery of the arcuately looped center of the looped rod,
the pubic base projection being sized and shaped to contact the top base surface of the male penis,
opposite side sections of the looped rod extended arcuately to a fulcrum curve of each opposite side section with each fulcrum curve positioned on a perineal area of a user at an opposite side of a perineal base of the male penis,
the looped rod is a metal coated with a cushioning material,
a lever arm extended from each fulcrum curve in an angular direction that is rearward and downward from the perineal base of the male penis and between legs of the user when the user is in a standing position,
a tension member attachment means on distal ends of the lever arms,
a tension member attachable to the lever arms,
a tension anchor attachable to the tension member and attachable to a hip section of the user, and
the tension anchor being a flexible belt attachable to a hip section of the user.

15. A penile engorgement valve as claimed in claim 14 wherein the tension member an elastic band.

16. A penile engorgement valve as claimed in claim 14 wherein the tension member is a plurality of elastic bands, the plurality of elastic bands being determined by pressure required at the fulcrum curves and at the arcuately looped center of the looped rod.

17. A penile engorgement valve as claimed in claim 14 wherein the tension member is a resilient strap.

18. A penile engorgement valve as claimed in claim 17 and further comprising:
a buckle with which the resilient strap is adjusted in length between the tension anchor and the lever arms and with which the resilient strap is attachable to the tension anchor.

19. A penile engorgement valve as claimed in claim 14 and further comprising:
a cushion pad positioned on the fulcrum curves between the looped rod and the perineal area of the user.

20. A penile engorgement valve as claimed in claim 14, wherein the cushioning material covering the looped rod encloses a fluid filled cavity.

* * * * *